United States Statutory Invention Registration [19]

[11] Reg. Number: H201

Yager [43] Published: Jan. 6, 1987

[54] BIOSENSORS FROM MEMBRANE PROTEINS RECONSTITUTED IN POLYMERIZED LIPID BILAYERS

[75] Inventor: Paul Yager, Washington, D.C.

[73] Assignee: United States of America, Washington, D.C.

[21] Appl. No.: 768,650

[22] Filed: Aug. 23, 1985

[51] Int. Cl.[4] ..... G01N 27/50

[52] U.S. Cl. ..... 436/151; 422/68; 422/98; 436/178

[56] References Cited

U.S. PATENT DOCUMENTS

| | | | |
|---|---|---|---|
| 3,966,580 | 6/1976 | Janata et al. | 204/195 B |
| 4,151,049 | 4/1979 | Janata | 204/1 T |
| 4,354,913 | 10/1982 | Pungor et al. | 204/195 P |
| 4,388,166 | 6/1983 | Suzuki et al. | 204/403 |

OTHER PUBLICATIONS

*Proc. Nat. Acad. Sci.* USA, vol 69, No. 12, pp. 3561–3566, Dec. 1972 "Formation of Bimolecular Membranes from Lipid Monolayers and a Study of Their Electrical Properties," M. Montal and P. Mueller.

*Pflugers Arch., 391,* 85–100 (1981) "Improved Patch–Clamp Techniques for High Resolution Current Recording from Cells and Cell-Free Membrane Patches," O. P. Hamill, A. Marty, E. Neher, B. Sakmann and F. J. Sigworth pp. 481–496.

*Science, 220,* 717–19 (1983), "Formation in Vitro Sperm Pronuclei and Mitotic Chromosomes Induced by Amphibian Ooplasmic Components" Vitaly Vodyanoy and Randall B. Murphy.

*Biophys. J., 47,* 93a (1985), "Patch Clamping of Bacteriorhodopsin and its Reconstitution in a Polymerizable Lechithin," Paul Yager.

*Ber. Bunsenges, Phys. Chem., 86,* 499–504, "Cyanine Dyes as Sensitizers of the Photopolymerization of Diacetylenes in Multilayers," C. Bubeck, B. Tieke, and G. Wegner (1982).

*Ber. Bunsenges, Phys. Chem., 86,* 495–498 (1982) "Self-sensitization of the Photopolymerization of Diacetylenes Studied in Multilayers," C. Bubeck, B. Tieke, and G. Wegner.

Angew. Chem. Suppl. 869–880 (1982), R. Benz, W. Press and H. Ringsdorf, "Black Lipid Membranes from Polymerizable Lipids".

"Reconstitution of Bacteriorhodopsin in a Polymerizable Lecithin" Paul Yager, submitted to Biochim. Biophys. Acta. Jul. 1985.

*Primary Examiner*—John F. Terapane
*Assistant Examiner*—Susan Wolffe
*Attorney, Agent, or Firm*—Robert F. Beers; William T. Ellis; Wendell R. Guffey

[57] ABSTRACT

A compact and portable biosensor which can detect the presense of an environmental stimulus is produced by extracting cell membrane proteins which are specific for the stimulus, purifying the proteins, and reincorporating the proteins into synthetic membranes. Electrodes are used to measure the voltage or current changes across the membrane when the proteins in the synthetic membranes react to the specific stimulus. The magnitude of the changes indicate the concentration of the stimulus in the environment.

15 Claims, 1 Drawing Figure

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

BIOSENSORS FROM MEMBRANE PROTEINS RECONSTITUTED IN POLYMERIZED LIPID BILAYERS

BACKGROUND TO THE INVENTION

This invention pertains generally to biosensors and more particularly to biosensors made by incorporating membrane proteins into polymerized lipid bilayers.

Biological cells have proteins in the cell membrane which react with molecules or other stimuli from outside the cell. The proteins sense the presense of an external stimulus and change the characteristics of the cell membrane, typically making the membrane more or less permeable to external molecules or ions. These proteins, therefore, function as biosensors for the cell by sensing the presence of stimuli in the cell's environment.

Many biophysical techniques have been developed to study the proteins which make up the membranes of biological cells. Among the most powerful of these techniques has been the isolation of membrane proteins, followed by reincorporation of the purified polypeptide into a synthetic membrane system in which the function can be studied in the absence of the frenetic activity which characterizes most native membrane preparations.

Reincorporation of proteins into synthetic membranes has most often been into vesicular membrane systems since they form spontaneously, provide an inside and outside aqueous space to probe, and can be stable for a long time. However, when access to the electrical activity of a membrane protein in a reconstituted system is required, most reconstituting vesicular membrane systems have compartments which are too small for convenient insertion of recording microelectrodes. The "black lipid membrane", or BLM, has offered an alternative solution. It allows transfer of protein from vesicles into a planar lipid bilayer separating two large aqueous compartments into which electrodes may be inserted for electrical measurement.

Montal and Mueller developed a method to form bilayers from monolayers on the surface of water. M. Montal and P. Mueller, *Proc. Nat. Acad. Sci. U.S.A.*, 69, 3561-3566 (1972). This method for making bilayers from monolayers (BFM) allows formation of bilayers in the absence of organic solvents which contaminate an otherwise cleanly-reconstituted system. As it is usually practiced, the method enables one to produce a bilayer patch half a millimeter or so in diameter. This technique is, however, frustrating even for its most avid advocates, and additionally, once formed, the bilayer is only stable for a few minutes or hours at the most.

Recently, a new method, the patch clamp technique, was developed. O. P. Hamill, A. Marty, E. Neher, B. Sakmann, F. J. Sigworth, *Pflugers Arch.*, 391, 85-100 (1981). In the patch clamp technique, a glass micropipette with a tip diameter of about 2 micrometers is placed against an existing bilayer or is moved through an air-water interface on which a monolayer exists. R. Coronado and R. Latorre, *Biophys. J.*, 43, 231-236 (1983). This technique results in the formation and sealing of a bilayer across the pipette tip. The resulting bilayer can have a resistance in excess of 10 gigaohms. Such a seal allows the recording of the current flow through single ion channels with time response in the sub-millisecond range. This technique has the major advantage over the BLM and BFM techniques that it is much easier to form bilayers on the glass pipette tips.

Although the lifetime of bilayers on the pipettes may be no longer than that in the BLM and BFM techniques, the ability to pull off the old pipette and put on a new one and immediately get a new working patch without having to clean out the apparatus makes the patch pipette technique far easier to use as a research technique. It has recently been shown that the glass of the pipette can be used to form good seals to artificial lipid monolayers on water, from which good patches form with useful electrical properties.

Many different membrane proteins have been monitored electrically using the above techniques. Among these are various neurotransmitter receptors, such as the acetylcholine receptor, visual proteins such as rhodopsin, and the bacterial proton pump bacteriorhodopsin. It has also been shown that sensory tissue, such as olfactory tissue, when presented to a BLM in such a manner that some of it is reincorporated into the bilayer, can induce an odor-dependent current flow across the membrane. V. Vodyanoy and R. B. Murphy, *Science*, 220, 717-19 (1983).

The generally short life of bilayers formed by all of the above-mentioned techniques has been an experimental annoyance that has hampered progress in the development of biosensors. Sensors produced with the above techniques would be easy to disrupt, mechanically limited to use in the laboratory, and have a short life span.

A lipid membrane is, therefore, needed which can be produced quickly and easily and overcome the poor longevity and durability of BLMs, BFMs, and patches. Improvement in the longevity and durability of the lipid membrane would provide a practical sensor which could be used in the laboratory and in the field.

SUMMARY OF THE INVENTION

It is, therefore, the object of the present invention to provide a polymerized lipid membrane which extends the longevity and durability of lipid bilayers used in biosensors.

It is another object of the present invention to provide a device which is portable and can be used in the field.

It is another object of the present invention to provide a quick and easy method for producing rugged biochemical sensors.

These and other objects are achieved by extracting membrane proteins from biological cells, reincorporating the proteins into a lipid bilayer, contacting the bilayer containing the membrane proteins with the environment containing the stimulus, and measuring the change in voltage or conductivity across the bilayer. The voltage or conductivity change indicates the presence of the stimulus and the magnitude of the voltage or conductivity change indicates the amount of the stimulus present. The polymerized lipid membrane provides a rugged suport for the proteins that function to sense molecules in the external environment.

In the preferred embodiment, the acetylcholine receptor protein is purified by affinity chromatography, reincorporated into lipid vesicles of polymerized lipids, and mounted on a glass microelectrode to produce a lipid bilayer containing the reincorporated proteins. One electrode from the silver-silver chloride pair is mounted on each side of the bilayer. The electrodes can measure the change in current across the bilayer when the acetylcholine receptor protein is effected by cholinergic agonists.

Other objects, advantages, and novel features of the present invention will become apparent from the following detailed description of the invention.

DETAILED DESCRIPTION OF THE INVENTION

Figure 1:
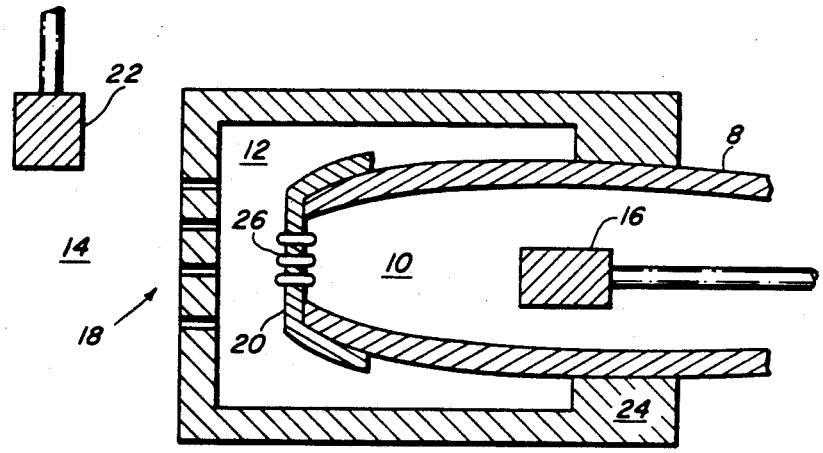
FIG. 1 is a diagram of a patch clamp-based biosensor for monitoring the concentration of chemicals in a solution.

A rugged biosensing device and method is disclosed which can be made specifically sensitive to any external stimulus such as vapors, dissolved compounds or other physical influence, for which there exists an appropriate membrane protein. Electrically active biological membrane proteins are isolated and subsequently reincorporated into planar lipid bilayers, preferably using polymerizable lipids. One or more bilayers are mounted on an appropriate device such that current and voltage changes across the membrane may be recorded. Binding of ligands to the proteins triggers either leakage of ions down concentration gradients or the pumping of charged ions from one side of the membrane to the other. A variety of proteins and mounting arrangements are possible including placement of the membrane at the end of a length of hollow optical fiber through which an electrode is passed. Such an electrode could be used for highly localized in vivo measurement of chemicals including neurotransmitters, drugs and toxins.

The sensor devices of the present invention consist of a polymerizable lipid bilayer (containing active membrane proteins) which separates two aqueous electrolyte-filled compartments. Each compartment contains a non-polarizable electrode which is used to sense the conductivity of the membrane. The polymerizable lipids form a bilayer in which the active membrane proteins that have been extracted from biological cells are reincorporated. The lipids must be compatible with the function of the protein, and in the completed device the lipids must be polymerized.

Many polymerized lipids have been synthesized and used for a number of research purposes. Bilayers of such lipids can be mechanically stronger, less susceptible to perturbation by solvents, and nearly unaffected by temperature. The stabilization is accomplished by converting the van der Waals forces which hold normal bilayers together to the covalent forces seen in the polymers. It has been shown that membrane proteins can function when reincorporated in vesicles of polymerizable lipids as monomers, and even after polymerization with UV light. P. Yager, *Biophys. J.*, 47, 93a (1985). It has also been shown that some polymerizable lipids can form stable patches, and BLMs. R. Benz. W. Press and H. Ringsdorf, *Angew. Chem. Suppl.* 869–880 (1982). They are logical candidates for the "ruggedization" of the reincorporated BLM, BFM or patch membrane system.

The polymerization itself may occur either before the device is assembled, or after the assembly. Polymerization can be by any means including chemical reactions, UV light, or with visible light after self-sensitization. C. Bubeck. B. Tiecke and G. Wegner, *Ber. Bunsenges. Phys. Chem.*, 86, 495–498 (1982) or in the presence of sensitizing dyes. C. Bubeck. B. Tiecke and G. Wegner, *Ber. Bunsenges. Phys. Chem.*, 86, 499–504 (1982). Visible and ultra-violet light are preferred, with visible light being most preferred. Any polymerizable lipid or mixture of polymerizable lipids with other non-polymerizable lipids can be used to form the bilayer but di-(10,12-tricosadiyuoyl) phosphatidylcholine and di-(10,12-uncosadiyuoyl) phosphatidylcholine are preferred. Other diacetylene-containing lipids including sulfolipids, polymerizable diene lipids, and polymerizable methacrylate lipids can be used to form the bilayer. Other heterogeneous combinations of non-polymerizable phospholipids and polymerizable lipids can also be used to form the bilayer. A pure polymerizable lipid, however, is most preferred.

The reincorporated active membrane proteins, which may be either pumps or gates, cause a change in conductivity in the membrane or pump charged particles across the membrane in response to molecules that effect the proteins. In either case, the membrane's conductivity can be monitored by either current flow across the membrane or a change in the voltage across the membrane.

The membrane patch is supported on a partition that may either be hydrophobic, as are those used in BLM and BFM technique, or hydrophilic, as is the glass pipette used in patch electrode work. The partition that supports the membrane defines two aqueous compartments, one of which may be accessible to the environment. A set of two electrodes, one on each side of the membrane, measures the current and/or voltage across the membrane. An appropriate electrical measuring device, such as those currently commercially available for patch clamping experiments, must be attached to the electrodes.

A shield which protects the fragile polymerized bilayer from mechanical contact with external surfaces is used to encase the membrane. Where the sensors are to be used in aqueous solutions, this shield might consist of simple porous screen or a semipermeable membrane such as a dialysis membrane. When the sensors are to be used to measure the concentrations of chemicals in air, the shield must keep the membrane wet while letting through the compound to be sensed. The basic function of the shield is to keep a specific environment close to the bilayer but to prevent damage to the bilayer.

A diagrammatic representation of a patch clamp-based biosensor to be used for monitoring the concentration of molecules in solution as shown in FIG. 1. The internal 10 and external 12 aqueous compartments are separated by the glass microelectrode tip 8 and the bilayer 20, which contains reincorporated active membrane proteins 26. The shield 24 protects the membrane and allows permeation of the relevant chemicals from the environment 14 into the membrane's external aqueous compartment 12 through a semipermeable section 18. Two silver-silver chloride electrodes 16, 22 allow electrical monitoring of the current flow through the membrane. For use of such an electrode for monitoring compounds from the air, the only modification would be that the external electrode 22 would be contained within the extra-membrane space 12 and that the shield 24 would not be permeable to water.

An example of a type of sensor which might be designed is one based on an acetylcholine receptor. In this sensor the receptor, AChR, would be purified by affinity chromatography and reincorporated into lipid vesicles of polymerized lipids. If the proper conditions are used the orientation of the protein in the liposomes can be better than 90% oriented in one direction. These vesicles would then be used to produce a high surface pressure monolayer at the air-water interface which can be used for preparation of bilayers on the electrode tip. The electrode used would be either a glass pipette pulled as in standard patch clamping technique, or a section of hollow glass fiber the tip of which would be pulled down to a 2 micrometer diameter opening. The desired orientation of the protein in the surface monolayer would be obtained by only passing the electrode once through the interface of the lipid-protein mixture, while the other pass of the electrode would be through a pure polymerizable lipid monolayer. While still under the surface of the buffer, the lipids would be polymerized, followed by the insertion of the tip of the electrode into a shield which simultaneously provides a mechanical barrier protecting the bilayer and also serves to create an isolated aqueous space outside the electrode interior. This space could be contained within a semipermeable membrane such as a dialysis membrane which would contain a solution of acetylcholinesterase. In this electrode system this enzyme would serve the function as does the acetylcholinesterase in the synaptic cleft i.e., to prevent the AChR from becoming saturated into the desensitized state in the constant presence of low levels of neurotransmitter.

This AChR electrode would respond with increased current flow through the membrane in the presence of cholinergic agonists, and, being composed of the same components as the post-synaptic membrane of the cholinergic synapse, would also detect antagonists and toxins for that system with the same specificity as the nerves themselves. The size of the electrode tip need only be a few microns in diameter as long as the semipermeable membrane containing the cholinesterase could be made that small. Such an electrode on the end of a hollow optical fiber could be inserted into a live animal or human to detect the levels of cholinergic agonists in vivo.

Several uses and advantages exist for this kind of sensor over those now in existence. A striking example is in case of detection of neutrotoxins such as organophosphates. The existing sensors often give false positives in the presence of non-toxic phosphate-containing compounds. A sensor based on the acetylcholine receptor and cholinesterase, such as the one we have described, would only respond to those compounds which are toxic to the tissue from which they are derived, i.e. nerve and muscle tissue.

The response of the detectors can be in milliseconds after the binding of the target chemical. Further, more than one type of membrane protein can be reincorporated in a single detector, making a single electrical measurement capable of detecting any of several chemicals of interest. The small size of the patch clamp pipette tip allows localization of the source of chemicals to within a few micrometers, if necessary. As previously mentioned, the polymerized bilayers may be mounted in any practical configuration to give low or high surface area depending on the needs of the detection scheme.

This class of devices has many different potential applications. A device could be produced by reincorporating proteins sensitive to the hazardous gases in workplaces. The device could provide a warning when toxic gases have escaped into the work environment. The device can also be used to conduct in vivo analysis for many different molecules by reincorporating a membrane protein that reacts to a molecule in the present in vivo. The size of the detector area could vary greatly with the type of application required. To produce a high current flow for easy detectability, a large number of proteins and consequently a large surface area would be required. Such large surface areas would be made possible by the strength of the polymerized bilayers. Alternatively, where small size detectors are preferable, it has been shown by the patch clamp technique that a 2 micrometer membrane size is adequate to produce measurable signals from as few as one protein molecule.

Obviously many modifications and variations of the present invention are possible in light of the above teachings. It is therefore to be understood that within the scope of the appended claims the invention may be practiced otherwise than as specifically described.

What is claimed and desired to be secured by Letters Patent of the United States is:

1. A method for detecting a stimulus such as vapors or dissolved compounds, comprising the steps of:

extracting membrane proteins which react to said stimulus from biological cells;

reincorporating said membrane proteins into a lipid bilayer, said bilayer being mounted so as to create an external compartment and an internal compartment, said external compartment being accessible to the environment containing said stimulus;

contacting said bilayer containing said membrane proteins with the environment containing said stimulus; and measuring the change in voltage or conductivity across said bilayer, said voltage or conductivity change indicating the presence of said stimulus, the magnitude of said voltage or conductivity change indicating the amount of said stimulus present.

2. The method of claim 1 wherein said lipid bilayer in said reincorporating step consists esentially of polymerizable lipids.

3. The method of claim 2 wherein said polymerizable lipids are selected from the group consisting of di-(10,12-tricosadiynoyl) phosphatidylcholine and di-(10,12-uncosadiynoyl) phosphatidylcholine.

4. The method of claim 1 wherein said membrane proteins in said reincorporating step are acetylcholine receptor proteins.

5. The method of claim 1 wherein said voltage or conductivity in said measuring step is measured using an electrode pair.

6. The method of claim 5 wherein said electrode pair is a silver-silver chloride electrode pair.

7. A biosensing device suitable for detecting a stimulus such as vapors or dissolved compounds, comprising:

means for supporting a lipid bilayer;

a lipid bilayer mounted on said supporting means, said suporting means and lipid bilayer creating an external compartment and an internal compartment, said external compartment being accessible to the environment containing said stimulus;

membrane proteins which react specifically to said stimulus, said membrane proteins having been extracted from biological cell membranes, purified, and reincorporated into said lipid bilayer;

means for facilitating the measurement of the current or voltage change across said lipid bilayer; and a shield that surrounds said supporting means and mounted bilayer for protecting said microelectrode and bilayer from external disruption, said shield having a semipermeable section in one end to allow access to the external environment.

8. The device of claim 7 wherein said lipid bilayer consists esentially of polymerizable lipids.

9. The device of claim 8 wherein said polymerizable lipids are selected from the group consisting of di-(10,12-tricosadiynoyl) phosphatidylcholine and di-(10,12-uncosadiynoyl) phosphatidylcholine.

10. The device of claim 7 wherein said means for supporting a lipid bilayer is a glass microelectrode.

11. The device of claim 7 wherein said means for facilitating the measurement of the current or voltage change across said lipid bilayer is an electrode pair.

12. The device of claim 11 wherein said electrode pair is a silver-silver chloride electrode pair.

13. The device of claim 7 wherein said membrane proteins are acetylcholine receptor proteins.

14. A biosensing device suitable for detecting a stimulus such as vapors or dissolved compounds, comprising:

a glass microelectrode having an opening at one end;

a polymerizable lipid bilayer for containing reincorporated membrane proteins mounted over said opening at one end of said microelectrode, said polymerizable lipid bilayer creating an internal compartment and an external compartment;

acetylcholine receptor membrane proteins which have been extracted from biological cell membranes, purified, and reincorporated into said polymerizable lipid bilayer;

a silver-silver chloride electrode pair, the first electrode of said pair being mounted in the internal compartment of said glass microelectrode, the second electrode of said electrode pair being mounted in the external compartment to said microelectrode tip, said external compartment being accessible to the environment containing said stimulus; and a shield surrounding said microelectrode tip and mounted bilayer for protecting said microelectrode and polymerized bilayer from external disruption, said shield having a semipermable section in one end to allow access to the external environment.

15. The method of claim 14 wherein said polymerizable lipids are selected from the group consisting of di-(10,12-tricosadiynoyl) phosphatidylcholine and di-(10,12-uncosadiynoyl) phosphatidylcholine.

* * * * *